US010847258B2

(12) United States Patent
Clark

(10) Patent No.: US 10,847,258 B2
(45) Date of Patent: Nov. 24, 2020

(54) SYSTEM, METHODS, AND APPARATUSES FOR MEDICATION RECORDS TRACKING

(71) Applicant: 4DA Inc., Littleton, CO (US)

(72) Inventor: David Clark, Littleton, CO (US)

(73) Assignee: 4DA Inc., Littleton, CO (US)

(*) Notice: Subject to any disclaimer, the term of this patent is extended or adjusted under 35 U.S.C. 154(b) by 0 days.

(21) Appl. No.: 16/415,990

(22) Filed: May 17, 2019

(65) Prior Publication Data

US 2019/0355451 A1   Nov. 21, 2019

Related U.S. Application Data

(60) Provisional application No. 62/672,711, filed on May 17, 2018.

(51) Int. Cl.
| | | |
|---|---|---|
| *G16H 10/60* | | (2018.01) |
| *G16H 10/40* | | (2018.01) |
| *G06F 21/62* | | (2013.01) |
| *G16H 80/00* | | (2018.01) |
| *G16H 20/10* | | (2018.01) |

(52) U.S. Cl.
CPC ............ *G16H 10/60* (2018.01); *G16H 10/40* (2018.01); *G06F 21/6245* (2013.01); *G16H 20/10* (2018.01); *G16H 80/00* (2018.01)

(58) Field of Classification Search
CPC ..................................................... G16H 10/60
See application file for complete search history.

(56) References Cited

U.S. PATENT DOCUMENTS

| | | | |
|---|---|---|---|
| 9,280,685 B2 | 3/2016 | Jackson | |
| 2006/0047538 A1* | 3/2006 | Condurso | G06F 19/326 705/3 |
| 2006/0125356 A1* | 6/2006 | Meek, Jr. | G06F 19/3462 312/215 |
| 2008/0140572 A1 | 6/2008 | Jackson | |
| 2009/0019552 A1* | 1/2009 | McLaughlin | G06Q 40/00 726/27 |
| 2012/0280049 A1 | 11/2012 | Bennett | |
| 2013/0054265 A1* | 2/2013 | Warner | G06Q 10/06311 705/3 |
| 2013/0191513 A1* | 7/2013 | Kamen | G06Q 10/00 709/219 |
| 2014/0150311 A1 | 6/2014 | Bacon | |
| 2016/0292386 A1* | 10/2016 | Finkelstein | G06F 19/3456 |

FOREIGN PATENT DOCUMENTS

WO   2009058163 A1   5/2009

* cited by examiner

*Primary Examiner* — John A Pauls
(74) *Attorney, Agent, or Firm* — Neugeboren O'Dowd PC

(57) ABSTRACT

A system for managing patient medical records comprises a medical records services and database platform, one or more patient physical tracking devices, and one or more healthcare provider scanning devices. The healthcare provider scanning devices are configured to enroll new patients into a medical records services and database platform by creating one or more enrolled patient physical tracking devices and scan one or more enrolled patient physical tracking devices. The system comprises one or more pharmacist scanning devices configured to scan the one or more enrolled patient physical tracking devices; scan information associated with a medication prescribed to an enrolled patient; and associate the enrolled patient with the medication via the medical records services and database platform.

20 Claims, 15 Drawing Sheets

SYSTEM, METHODS, AND APPARATUSES FOR MEDICATION RECORDS TRACKING

PRIORITY

The present Application for Patent claims priority to Provisional Application No. 62/672,711 entitled "SYSTEM, METHODS, AND APPARATUSES FOR MEDICATION RECORDS TRACKING" filed May 17, 2018, and assigned to the Assignee hereof, the entire contents of which are hereby expressly incorporated by reference herein.

FIELD OF THE DISCLOSURE

The present disclosure relates generally to electronic medical records. In particular, but not by way of limitation, the present disclosure relates to systems, methods and apparatuses for securely and confidentially recording and communication of prescription drug records between patient health care providers.

BACKGROUND OF THE DISCLOSURE

In our current healthcare system, patients, healthcare providers, and other stakeholders face many challenges related to the provision of prescription drugs. Patients often struggle to remember the names of medications they currently take or have taken in the past, let alone their dosages, indications, or interactions. Some patients struggle with compliance with dosing regimens, while others struggle with addiction to opioids and other painkillers.

Healthcare providers face challenges in knowing the prescription drug history of new patients, primarily because transferring electronic medical records (EMR) from one provider to another is often deterred by incompatibility between EMR systems. Though all healthcare providers have been encouraged to transition from paper to EMR in recent years, the market for EMR systems has been made up of numerous competing entities with proprietary systems that are extremely difficult to integrate or transfer between. As a result, when providers see new patients whose prescription histories are unknown, providers may waste time trying medications that have previously not worked for patients.

Pharmacies usually have accurate lists of patients' information for patients whose prescriptions the pharmacy has filled before or who are otherwise in the pharmacy's system. However, new or transferring patients may not have all their current or past medications listed in a particular pharmacy's database. Some systems are currently in place for some level of monitoring of controlled prescription drugs (which may also be referred to as "controlled substances" or "scheduled" medications). Currently, every state has a prescription drug monitoring program through which controlled prescription drugs are tracked. Though pharmacies may be able to see whether a new patient has been prescribed controlled prescription drugs, other drugs may not be associated with a particular patient's record. Pharmacies are often the primary checker for harmful drug interactions, so any missed records of a patient's current or past prescriptions can potentially be dangerous.

Emergency department and urgent care providers face additional unique challenges when they don't have access to accurate patient prescription drug information. In emergency situations, having accurate and quick ways to access a patient's medication list can assist emergency department physicians in making correct diagnoses of patients' conditions. Quick and accurate diagnoses can be the difference between life and death in some situations. In emergency departments, patients or their caretakers ideally have a list of medications or prescription vials. However, in situations in which these options are not available, a hospital employee (doctor, pharmacist, pharmacy technician, or nurse) will have to do medication reconciliation, which is a tedious and time consuming process where one either has to call a patient's pharmacy or family member. In emergencies, medication reconciliation can be the time limiting step in making an appropriate diagnosis.

A number of other obstacles have prevented universal, secure, fully integrated prescription records systems from being implemented; namely, high legal requirements for protecting confidential patient information (i.e., the Health Insurance Portability and Accountability Act "HIPAA"), competition between existing medical records providers, and incompatibility between systems of various stakeholders, to name just a few. Therefore, a need exists for systems, methods, and apparatuses that can remedy current problems.

SUMMARY

An aspect of the present disclosure provides a system for managing patient medical records. The system may comprise a medical records services and database platform, one or more patient physical tracking devices, and one or more healthcare provider scanning devices. The healthcare provider scanning devices may be configured to enroll new patients into a medical records services and database platform by creating one or more enrolled patient physical tracking devices and scan one or more enrolled patient physical tracking devices. The system may further comprise one or more pharmacist scanning devices configured to scan the one or more enrolled patient physical tracking devices; scan information associated with a medication prescribed to an enrolled patient; and associate the enrolled patient with the medication via the medical records services and database platform.

Another aspect of the present disclosure provides a method for managing patient medical records, the method may comprise enrolling new patients into a medical records services and database platform by creating one or more enrolled patient physical tracking devices. Then, the method may comprise scanning, with one or more pharmacist scanning devices, the one or more enrolled patient physical tracking devices and information associated with a medication prescribed to an enrolled patient. The method may then comprise associating the enrolled patient with the medication via the medical records services and database platform.

DETAILED DESCRIPTION

Figure 1:
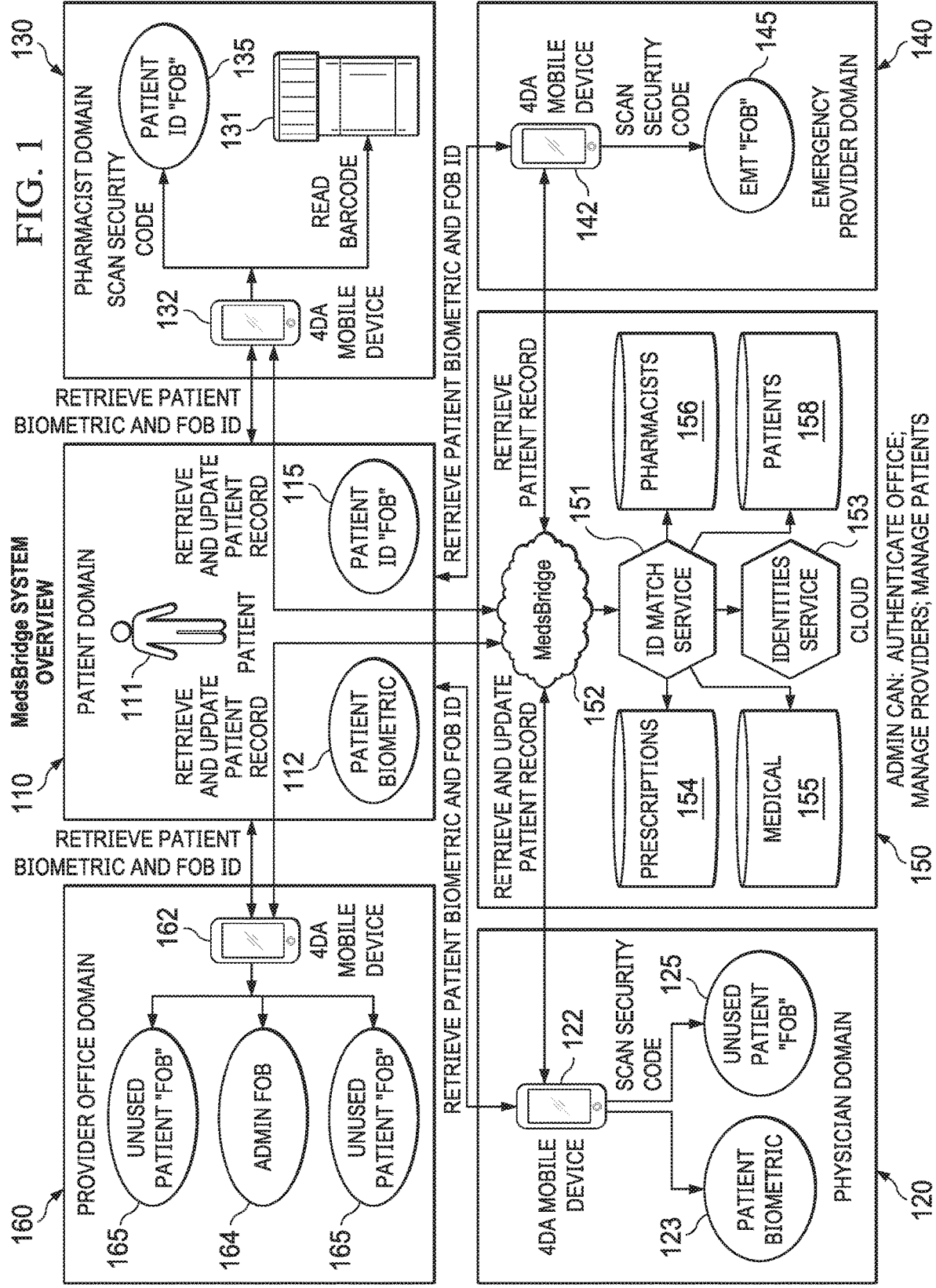
FIG. 1 is an overview of a system of the present disclosure.

The word "exemplary" is used herein to mean "serving as an example, instance, or illustration." Any embodiment described herein as "exemplary" is not necessarily to be construed as preferred or advantageous over other embodiments.

The system of the present disclosure comprises several components, including physical hardware components and software components, which together provide a universal prescription medication reporting system, which may be referred to herein as "the system," or alternatively, "the software platform" or simply "platform." A first component of the system is a physical tracking device for patients. A second component is a similar physical authentication device for healthcare providers. These devices may be implemented as a read-only "dumb" electronic ID device that provides some kind of unique identifier (i.e., unique to the device) but which itself does not retain any personally identifying information about a particular patient. These devices may electronically transmit their unique identifier through one or more types of proximity-based scanning technologies, such as RFID, QR code, Near Field Communication, magnetic card, BLE, or any other similar type of proximity-based scanner. These devices may be referred to herein as "fobs" and may be implemented in any type of small, portable device, such as a unique hardware device created specifically for the system of the present disclosure, or a plastic card, wearable device, keychain device, or similar hardware. Throughout the disclosure, fobs may be referred to as "patient fobs" or "provider fobs," or more specific types of fobs depending on the particular device and its role in the system.

Another component of the system may comprise a scanning device for reading the fob. Yet another component of the system comprises a software application executed on the scanning device. In many embodiments, the software application may be an embedded application on a dedicated mobile device. For example, in embodiments, the scanning device may be implemented in a commercially available smartphone with some or all of its standard application software removed and replaced with embedded (or, in some embodiments, downloadable) software for implementing the system of the present disclosure. Commercially available smartphones may be used in this way because they have cellular data and Wifi connectivity hardware as well as electronic scanning hardware (e.g., NFC and BLE radios) for implementing aspects of the system. In other embodiments, a unique, customized hardware scanning device having embedded or downloadable software may be used.

It is contemplated that regular healthcare providers, pharmacies, and emergency healthcare providers may each have access to a particular version of the scanning device/software application combination in the present system. Each of the versions may be equipped with particular functions and permissions that the other versions do not have for security and privacy purposes. Throughout the disclosure, these versions may be referred to as "physician scanning devices," "pharmacist scanning devices," and "emergency scanning devices," and should each be construed to mean the hardware scanning devices and the software executed thereon, each in their respective healthcare-providing environments.

An aspect of the present disclosure is that each patient fob has a unique identifier but does not contain any patient health information (PHI) itself. A physician scanning device may uniquely perform two main functions: 1) enroll new patients in the system with new patient fobs, thereby associating patients with the patient fobs within the software platform and 2) scan existing patients' fobs to retrieve their past prescription data. A pharmacist scanning device may perform three different main functions: 1) scan the fob of an enrolled patient to authenticate and identify the patient through the system, 2) scan a barcode of a prescribed drug for that patient, and 3) associate the patient with the prescribed drug in the system. An emergency healthcare provider scanning device may, in embodiments, perform only one function of scanning the fob of an enrolled patient to authenticate and identify the patient through the system and view a patient's medications history.

Physicians may have many unassigned fobs at their disposal and may enroll each new patient that they see by scanning a new fob. It is contemplated that only physicians, or alternatively, only physicians and pharmacists, may enroll patients in the system. The enrollment process is designed to be secured via various methods, network architectures, and encryption and authentication steps. In particular, the system of the present disclosure utilizes the software executed on the physician and/or pharmacist scanning devices to authenticate and then receive PHI that is stored remotely in one or more secure servers. That is, neither the patient fob nor the physician, pharmacist, and emergency healthcare provider scanning devices stores any PHI. PHI may be only stored at the one or more remote, secure servers of the platform and transmitted to an interface (i.e., GUI) accessible to the physician, pharmacist or emergency provider. This PHI may be transmitted only upon authentication, which is initiated via the scanning of both the patient fob along with a unique provider fob—a physician, pharmacist, or emergency healthcare provider fob, as will be described presently—and completed via additional steps.

Because the PHI is stored and accessed as described, PHI can remain secure even if a patient loses a fob, or if someone tries to fraudulently access a patient's information by stealing a fob or accessing a scanning device. Because enrollment is only done by physicians (and/or pharmacists, in some embodiments), physicians and pharmacists can require in-person use of the fob along with another form of ID to confirm the identity of the patient when enrolling a patient, prescribing medication, or dispensing medication. It is contemplated that identification requirements at various healthcare provider interaction points may remain the same as they are without the system of the present disclosure. For example, family members may often pick up prescriptions for patients, and identification is typically not required at pharmacies to pick up medication in such circumstances. However, some types of prescriptions, such as opioids, do require patient identification and are currently tracked through some state-mandated prescription drug reporting systems. No matter what the current identification requirements for particular prescriptions are, it is contemplated that the system of the present disclosure can be used concurrently. Patients may still have family members pick up medication in cases where such an action is already permissible, but may give their fobs to such family members for scanning. If a patient must be present or provide personal identification, such as a driver's license, the patient may present his or her own fob. Use of the fob at the pharmacy allows a new drug to be associated with the patient, as will be described in this disclosure.

As previously mentioned, PHI may be transmitted from one or more servers to an interface for a physician, pharmacist, or emergency healthcare provider. The interface may be referred to herein as a "portal" and may be implemented as software-as-a-service or downloadable software on any kind of computing device, or may be available as part of the scanning device software. It is contemplated that each type of user's portal may have different features and functions; for example, there may be a physician portal, a pharmacist portal, and an emergency healthcare provider portal. In some embodiments, the system may comprise a patient portal as well. The physician portal, pharmacist portal and emergency healthcare provider portal may each be accessible via the physician scanning device, pharmacist scanning device, and emergency healthcare provider scanning device, respectively, in embodiments.

FIG. 1 shows an overview of the system 100 of the present disclosure as previously described. The system 100 is depicted in terms of its various "domains" and other network components used to implement the platform. As shown, the system 100 comprises a patient domain 110, a physician domain 120, a pharmacist domain 130, and an emergency healthcare provider domain 140, and a provider office domain 160. Further, the system comprises a cloud component 150, which itself comprises a cloud server-based application 152, a plurality of cloud server-based services 151 and 153, and a plurality of databases 154, 156, and 158. The cloud component may be referred to herein as a medical records services and database platform Embodiments of the system 100 may comprise additional and/or different services and databases, but as shown, the system 100 comprises an ID match service 151, an Identities Service 153, a prescriptions database 154, a medical records database 155, a pharmacists database 156, and a patients database 158. Each component will be described in further detail throughout the disclosure.

Each component of the system 100 may be designed to be vendor agnostic and/or vendor neutral. That is, the fobs, devices, and servers may be used and accessed by any healthcare provider, pharmacy, or patient no matter what kind of insurance plan, medical group, pharmacy benefit manager, electronic medical records vendor, or other organization with which a stakeholder is affiliated. In particular, any fob, including existing ones, which have unique identifiers, may be used with the platform.

In the physician domain 120, a provider/physician may use a physician scanning device 122 to enroll a new patient with a new patient fob 125. The new patient enrollment process is described in detail with reference to FIG. 2, but in general, a physician will scan the fob 125 to obtain its unique identifier, then receive the patient's PHI from the patient him or herself (e.g., through an in-person verbal or written intake process). Then, the physician may scan his or her own previously-assigned physician fob, which acts as an authentication factor. Throughout this system, physicians, pharmacists, and emergency healthcare providers each have their own fobs in order to provide an authentication step whenever a patient fob is scanned, essentially implementing two-factor authentication—one factor associated with the patient and the second factor associated with the provider. It is contemplated that the system administrator (i.e., the company providing the system) may enroll physicians, pharmacists, and emergency providers with these fobs. This enrollment process may require particular stringent identification and secure enrollment steps given the authority these participants have to submit and receive PHI within the system. In embodiments, these provider fobs may have additional features not included in patient fobs, or they may be identical types of devices as the patient fobs with identical functionality and their own unique identifiers.

In embodiments, authentication may involve patient biometric identification, either in addition to, or in place of, a patient fob. Biometric identification, for the purposes of the present disclosure, may include any uniquely identifying physical feature or attribute of a human person, including, but not limited to, fingerprints, retina scans, facial recognition, or other types of identification known in the art or those yet to be developed. FIG. 1 shows that a patient 111 may use the patient fob 115 and/or the patient biometric 112 for authentication within the system. At enrollment, as shown in the physician domain 120, the physician scanning device 122 may be used to detect, accept, and enroll the patient into the system. This information may be transmitted and stored at the cloud service 150 in the patient database 158. It is contemplated that the pharmacist scanning device 132 and the emergency provider scanning device 142 may be able to detect a patient biometric 112 and use it to authenticate the patient's identity via the cloud server. In implementations, users of the system may choose to require both patient biometrics and patient fobs for high-security authentication.

In embodiments, an administrator within a provider office domain 160 may also be used to authenticate the office itself, enroll and manage providers, and enroll and manage patients. It is contemplated that an administrator at a provider office can implement the various safety and security protocols required to enroll providers in the system, and can be one point of contact for interacting with the system provider. As shown in FIG. 1, an administrator may have an administrator scanning device 162, an administrator fob 164, and a plurality of unused patient fobs 165 to enroll future patients. The devices in the provider office domain 160 may function similarly to corresponding scanning devices and fobs described throughout the system.

Still referring to the physician domain 120, the physician may then associate the patient fob identifier with the PHI, and send it to the application 152 for storage. It is contemplated that the PHI is not stored in the physician's scanning device 122 in many embodiments. However, the physician may temporarily receive and view a patient's prescription drug history through the physician portal (after authentication). This allows a provider to see what prescription medication the patient may have been prescribed in the past in order to assist in future diagnoses and prescribing.

In the patient domain, the patient 111 retains the patient fob 115 for future use in recording his or her prescription drug records. Though the patient's PHI is now stored in the cloud component 150, the patient 111 does not have any PHI stored on the patient fob 115.

A physician or other healthcare professional with prescription authority may prescribe medication to the patient in a customary manner. Many prescribers still utilize paper prescriptions, while others call them into pharmacies or utilize electronic prescribing systems to transmit prescriptions to pharmacies. The system of the present disclosure does not require the entry of a prescription from a prescriber into any part of the platform; that is, the system can be used alongside all currently-existing prescribing methods. However, it is contemplated that the platform may be used to electronically transmit prescriptions from a prescriber to a pharmacy in some embodiments by being integrated with electronic prescribing systems.

Once a physician prescribes medication to the patient 111, the patient 111 may bring the fob 115 to a pharmacy. In the pharmacy domain 130, the pharmacist 131 may receive the patient's prescription in a customary manner (i.e., paper, call, or electronic). Then, the pharmacist 131 may scan his or her own pharmacist fob 135 and the patient fob 115 via a pharmacist scanning device 132, and then scan a bar code on the prescription medication 136 itself. The pharmacist fob 135 acts as an authentication factor; both the pharmacist fob 135 and the patient fob 115 are required to send and receive the patient's prescription drug information. The pharmacist 131 may then associate the patient fob identifier with the prescription medication 136 on the pharmacist scanning device 132. The prescription medication 136 may then be transmitted and stored to the cloud component 150, where it may be permanently associated with the PHI associated with the scanned patient fob 115. This system thereby associates a particular patient with the patient's prescription drug history and stores it at the cloud component 150. It is contemplated that a single patient, and therefore, the patient's PHI, may be associated with multiple fob devices. For example, a patient may use a wearable one for emergencies and a keychain one for convenience, or a patient may lose a fob and need a new one, or a patient may forget his or her fob when coming to an appointment and need an additional one. In these cases, providers may associate new patient fobs with an existing patient. The identity service 473, shown in FIG. 4, may look up the patient's PHI via any fob associated with the patient and associate the correct prescription medication with the actual patient record.

It is contemplated that the pharmacist scanning device 132 may not store the patient's PHI or prescription drug information in many embodiments, but that the pharmacist scanning device 132 may receive the patient's PHI and/or prescription drug information temporarily, after scanning the pharmacist and patient fobs and subsequent server authentication. This allows a pharmacist to see (via the pharmacist's portal) other medications the patient may be on simultaneously in order to help identify potentially harmful drug interactions.

At the emergency provider domain 140, an emergency provider 141 may have an emergency scanning device 142 for scanning the patient fob 115. Upon a patients' arrival at the emergency provider, the emergency provider 141 can scan the patient's fob 115 and the emergency provider's fob 145, again providing two-factor authentication in order to transmit the scanned fob unique identifier and receive the patient's prescription drug history via the emergency provider portal. Being able to access a complete history of medication the patient has been prescribed can be crucial in assisting in diagnosis of a condition or treatment thereof. For example, an emergency provider can find out if an unconscious patient likely overdosed, or took something that adversely interacted with a current medication. If a patient is confused or unresponsive, the provider can still look to the prescription drug record to ascertain what conditions the patient may have based on the medications previously prescribed. For example, medications for heart disease, high blood pressure, or diabetes could provide clues to present emergency symptoms. The provider can also avoid administering additional medication that would harmfully interact with current medication.

Because the prescription drug record can be so helpful in emergency situations, especially for unconscious patients, it is contemplated that certain high-risk patients may want to use a fob implemented in an easily-accessible wearable device, such as a bracelet, necklace, or the like. For example, elderly patients, those who live alone, those who suffer from addiction, or those with chronic disease may especially benefit from ensuring that their prescription drug record is readily accessible via a wearable fob.

Figure 2A:
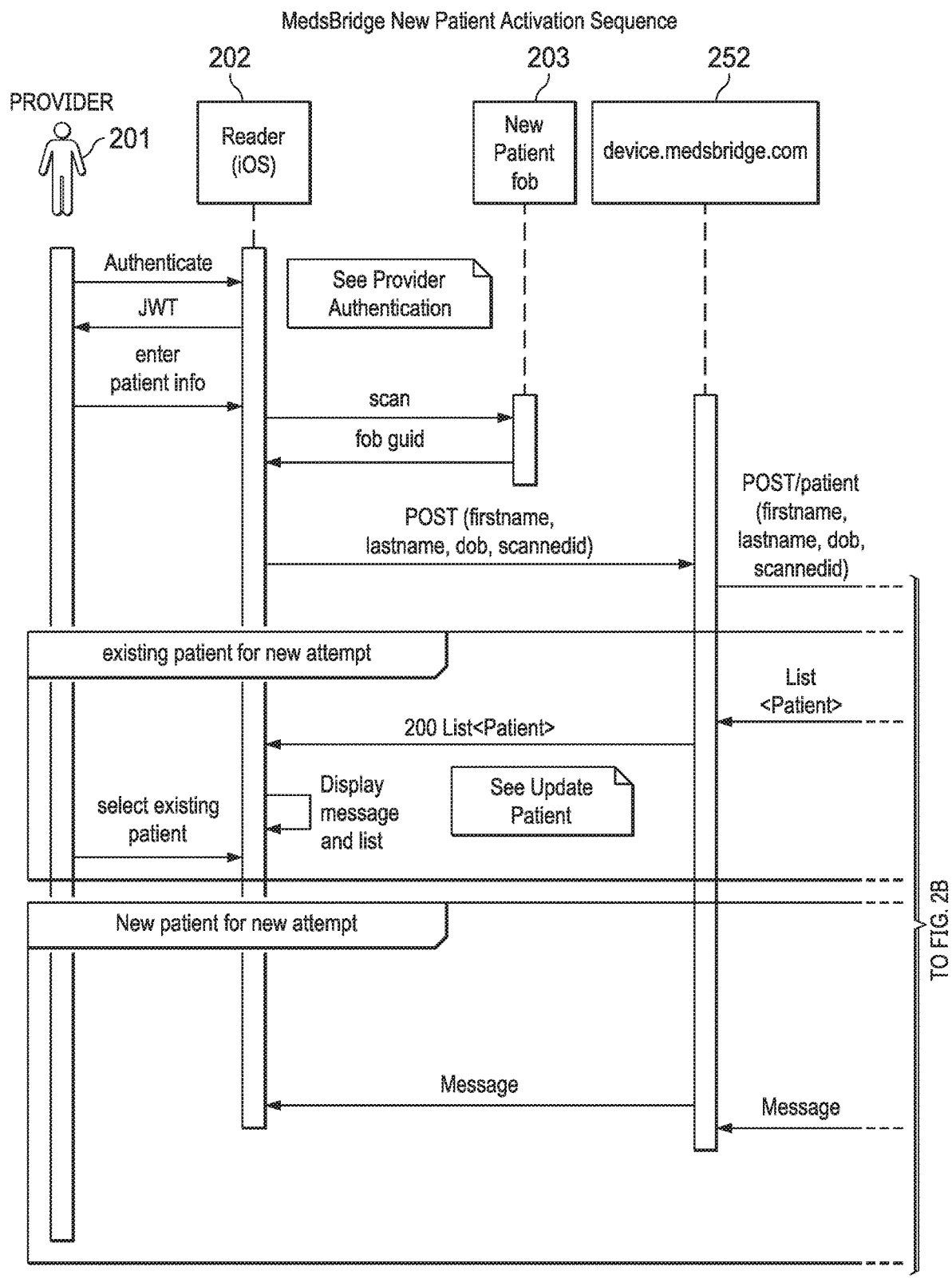
FIGS. 2A and 2B show a logical block diagram of a patient activation sequence according to the present disclosure.
Figure 2B:
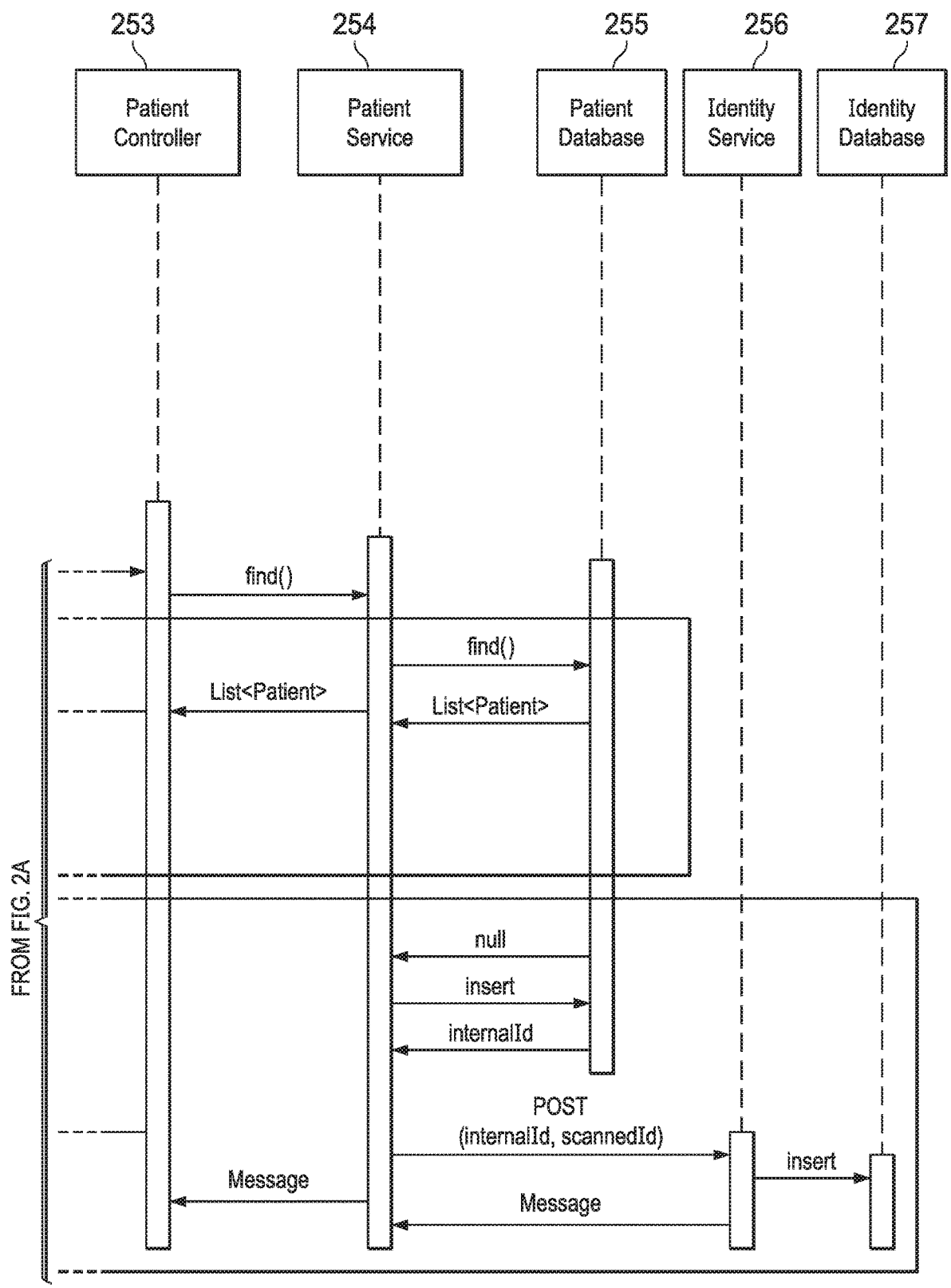

The subsequently described figures show specific embodiments of processes and sequences of the present disclosure. It is contemplated that other embodiments may deviate from the processes and sequences shown without departing from the scope of the present disclosure. FIGS. 2A and 2B show a new patient activation sequence 200 in accordance with an embodiment of the present disclosure. The new patient activation sequence 200 shows how data is authenticated, transmitted, and received via various system components as shown in FIG. 1. As shown, information is transmitted and received to and from the application 252, the patient controller 253, the patient service 254, the patient database 255, the identity service 256, and the identity database 257. It is contemplated that different pieces of PHI may be stored at separate servers and/or database, and may be manipulated, encrypted, and transmitted through various services in order to increase information security.

Figure 6A:
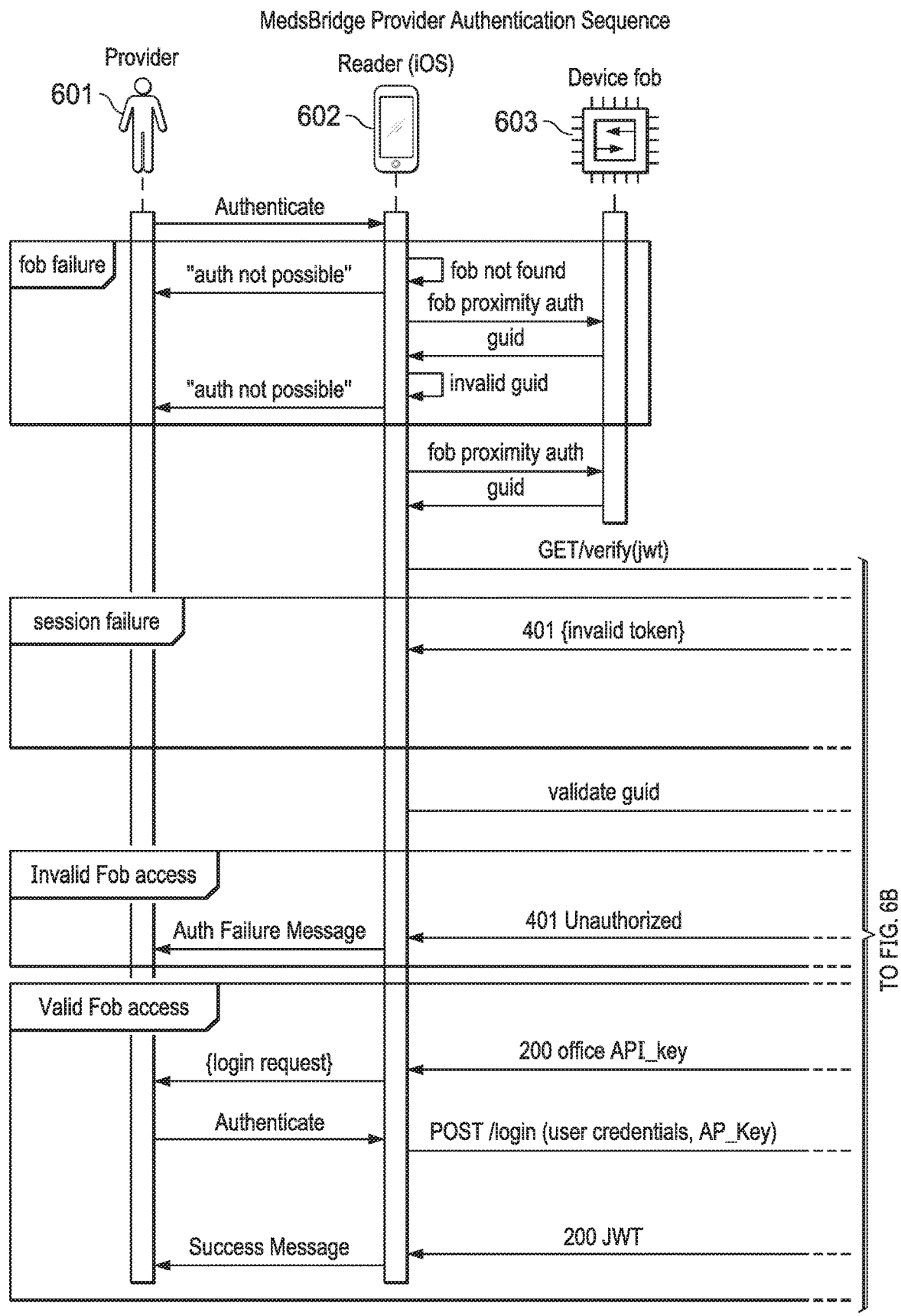
FIGS. 6A and 6B show a logical block diagram of a sequence for healthcare provider authentication according to the present disclosure.
Figure 6B:
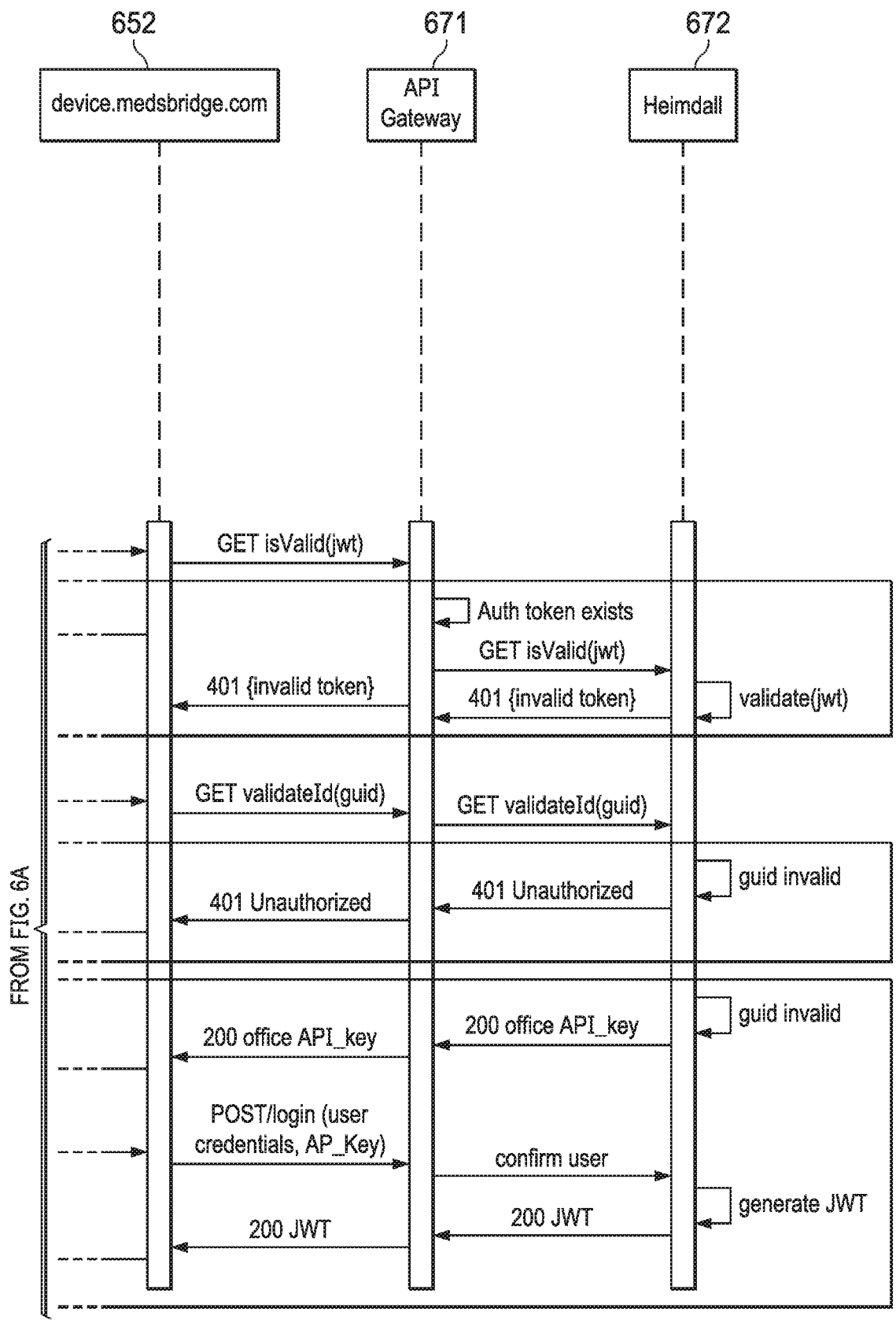

As shown, the provider 201 may have both a reader having downloadable, installed, or embedded software (also referred to as a scanner) 202 through which he or she may enroll a new patient with a new patient fob 203. The provider may first authenticate his or her own identity via a provider authentication protocol, which may comprise scanning his or her own fob, using biometric authentication, entering a password, or some other type of authentication. FIGS. 6A and 6B, which will be described later in the disclosure, provides an overview of the provider authentication sequence. The provider 201 may enter the patient info into the reader 202, which may also accept biometric identification from the patient in embodiments. The reader may send back a security tracking token (e.g., a JSON Web Token as shown in FIG. 2) to determine if a request is authenticated within an appropriate time frame. The reader 202 may then scan the new patient fob 203, which transmits the "fob guid" (a unique ID of the fob) back to the reader 202. The reader 202 may then transmit both the patient information, such as first name, last name, and date of birth, plus the scanned ID from the fob 203 to the system application 252, which may be in the cloud. This patient information may be searched via the patient controller 253, the patient service 254, and/or the patient database 255. If the patient is found in the system, the listing of the patient may be returned to the reader 202, which will display to the provider 201 that the patient already exists and allow the provider 201 to select the patient. This sequence may be used to associate a new fob with a patient who has lost a previously enrolled fob. In other embodiments, this sequence may be used to associate a fob with a person authorized to pick up medication for a patient (e.g., a family member or care taker).

If the patient is not found in the patient database 255, the patient service 254 may add the patient to the patient database 255, and the patient database 255 may provide an internal ID back to the patient service 254. The patient service 254 may then provide the associated internal ID and scanned ID to the Identity Service 256, which may then write the record of the associated internal ID and scanned ID to the Identity database 257. It is contemplated that the different pieces of information associated with a particular patient, including the personally identifying information (e.g., name, date of birth, social security number), the scanned ID, and the internal ID, may not all be stored at the same database for security and compliance reasons. For example, the personally identifying information may be stored at the Patient Database 255, but only the internal ID and scanned ID may be stored at the Identity Database 257. Because the various pieces of data are separated across the different databases, a single data breach will not expose any useful data.

Figure 3A:
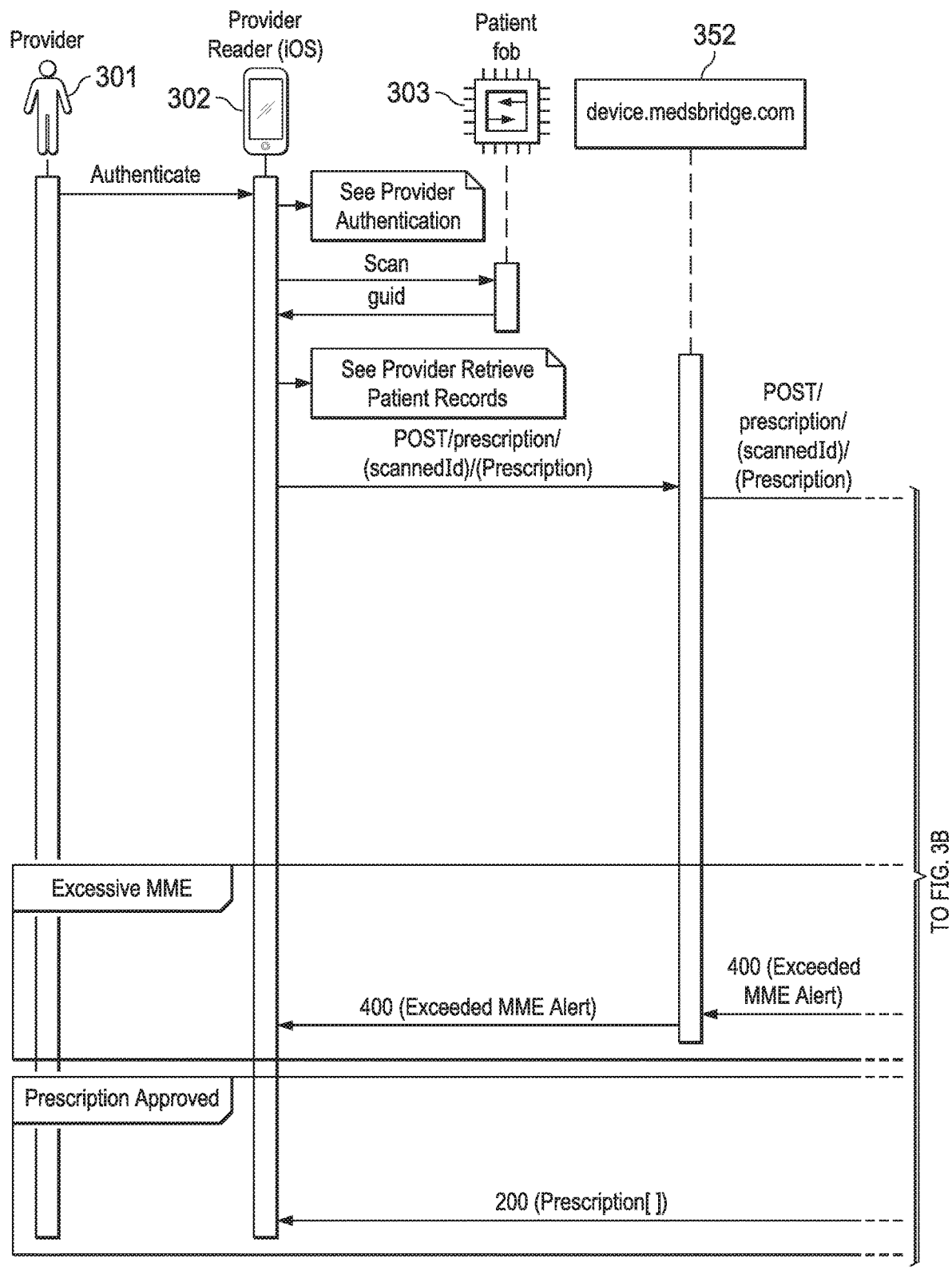
FIGS. 3A, 3B, and 3C show a logical block diagram of a sequence for a medical provider updating a patient records according to the present disclosure.
Figure 3B:
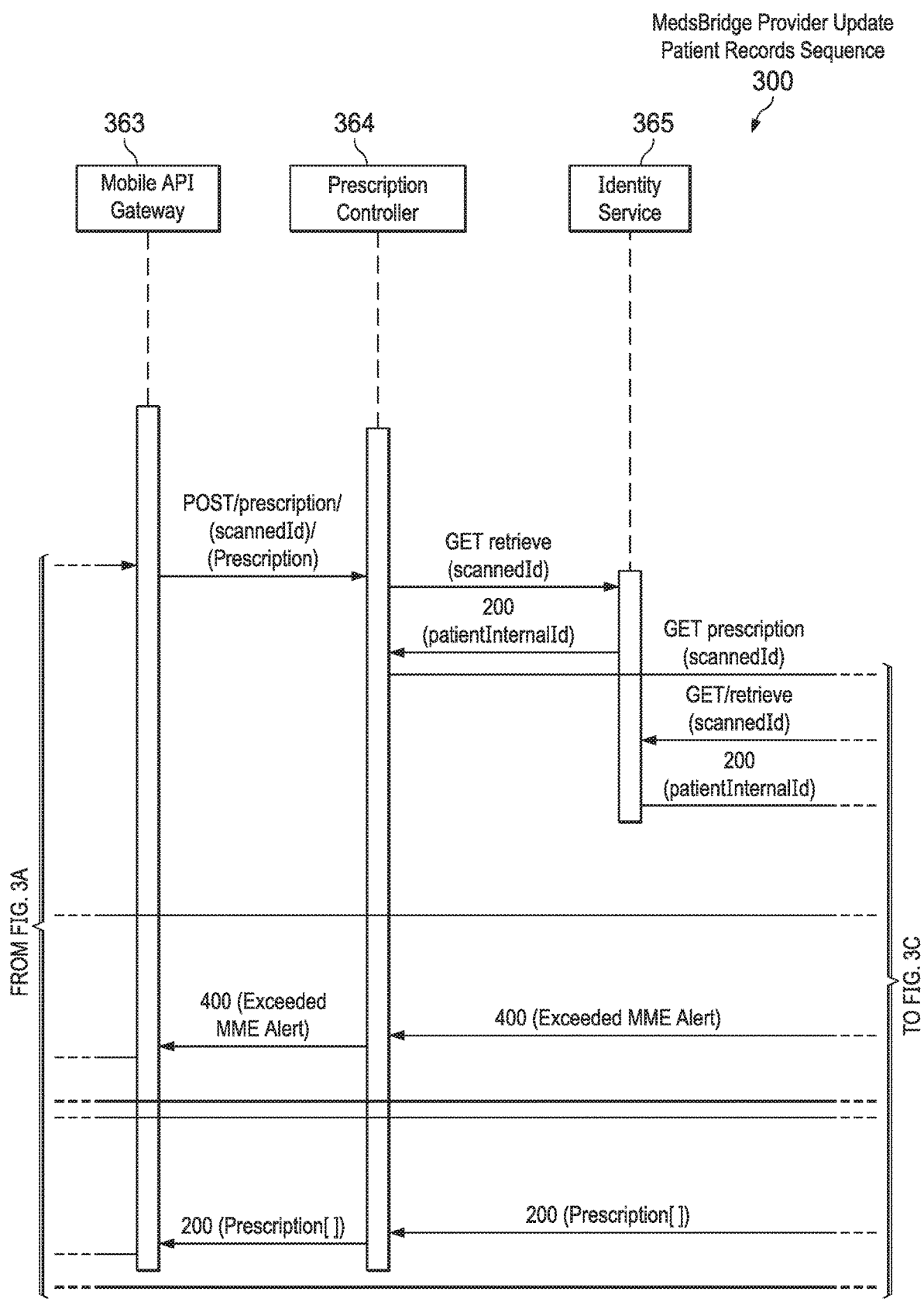
Figure 3C:
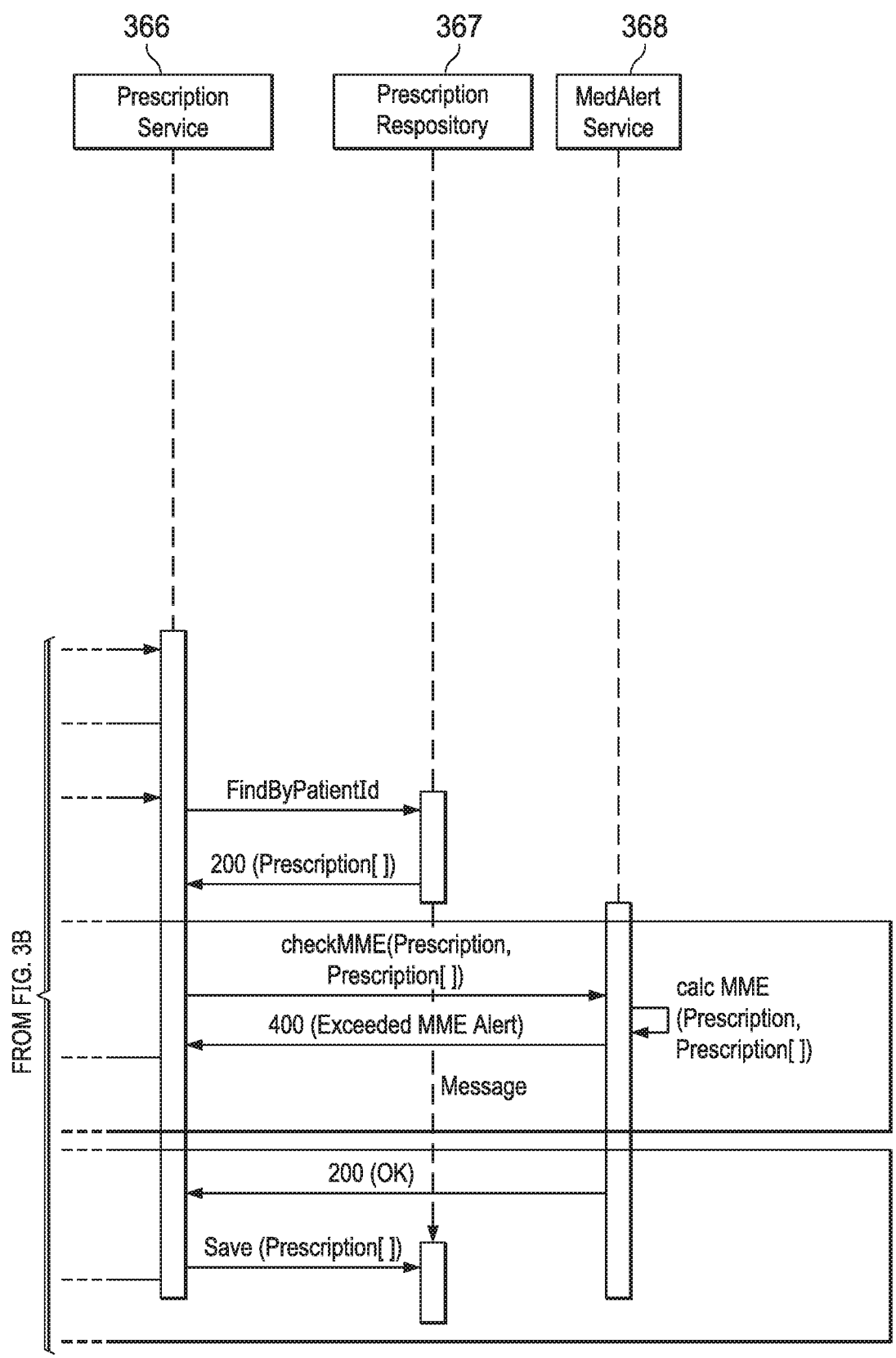

FIGS. 3A and 3B show a provider update patient records sequence 300, which may be implemented to add new prescriptions to a patient's prescription drug record. As shown, information may be authenticated, transmitted, and received via the application 362, the mobile API gateway 363, the prescription controller 364, the identity service 365 (which may be the same or different from the identity service 256 of FIG. 2), the prescription service 366, the prescription repository 367, and the med alert service 368. The med alert service 368 may calculate a "milligram morphine equivalent" ("MME") for a particular list of drugs, which is information that can be used to indicate dangerous dosage levels of drugs on the particular list. In embodiments, aspects of the med alert service 368 may be used to provide other potentially dangerous drug interaction information.

As shown, the provider 301 may first authenticate his or her identity at the reader 302 using methods previously described. Then, the provider 301 may scan the enrolled patient fob 303, which provides its scannable ID ("guid") to the reader 302. The provider 301 may enter the prescription into the reader 302, which may then send the prescription plus the scanned ID to the system application 362. The prescription plus the scanned ID may serve to associate the prescribed medication with the patient. This prescription plus the scanned ID may then be sent through an API gateway 363 to a prescription controller 364. The API gateway 363 may authenticate and route all the different requests received in each of the sequences shown and described. The prescription controller 364 may then make a call to the identity service 365 (which may be the same identity service 256 from FIG. 2) using the scanned ID to retrieve the patient internal ID. In this sequence, it may not be necessary for any patient personally identifying information to be transmitted, which provides the benefit of security and compliance. Then, the prescription controller 364 may send the prescription plus the scanned ID to a prescription service 366, and the identity service 365 may simultaneously, or shortly thereafter, send the patient internal ID to the prescription service 366.

The prescription service 366 may then look for the patient internal ID within a prescription repository (i.e., database) 367, which may comprise all previously stored prescriptions associated with the patient internal ID. Any previously stored prescriptions may then be sent from the prescription repository 367 back to the prescription service 366. The prescription service 366 may then send the new prescription information plus the previously stored prescriptions to a medical alert service 368 for identifying and/or calculating dangerous drug interactions. Such a medical alert service may be implemented by a third-party service provider. If the medical alert service 368 calculates an excessive dosage (e.g., via the MME method) and/or a potentially dangerous interaction, the service will transmit an alert through one or more of the prescription service 366, the prescription controller 364, the mobile API gateway 363, and the system application 362 to the reader 302 to indicate that the prescription is not approved. If no such alert is generated from the medical alert service 368, an approval may be sent from the medical alert service 368 to the prescription service 366. The prescription service 366 may then save the new prescription in the prescription repository 367 (with the patient internal ID) and send the prescription approval through one or more of the prescription controller 364, the mobile API gateway 363, and to the reader 302.

Figure 4A:
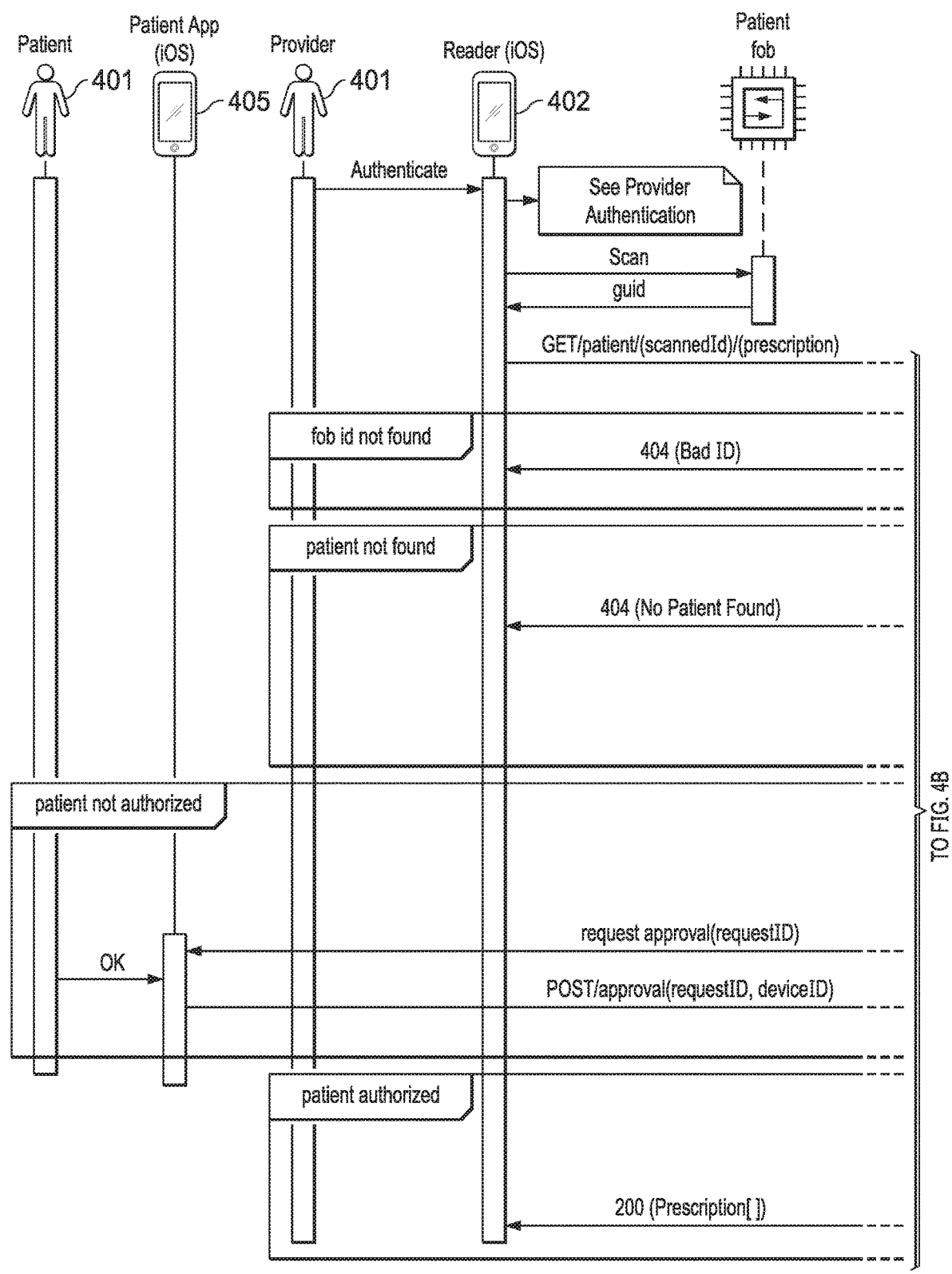
FIGS. 4A, 4B, and 4C show a logical block diagram of a sequence for a medical provider or pharmacist retrieving patient records according to the present disclosure.
Figure 4B:
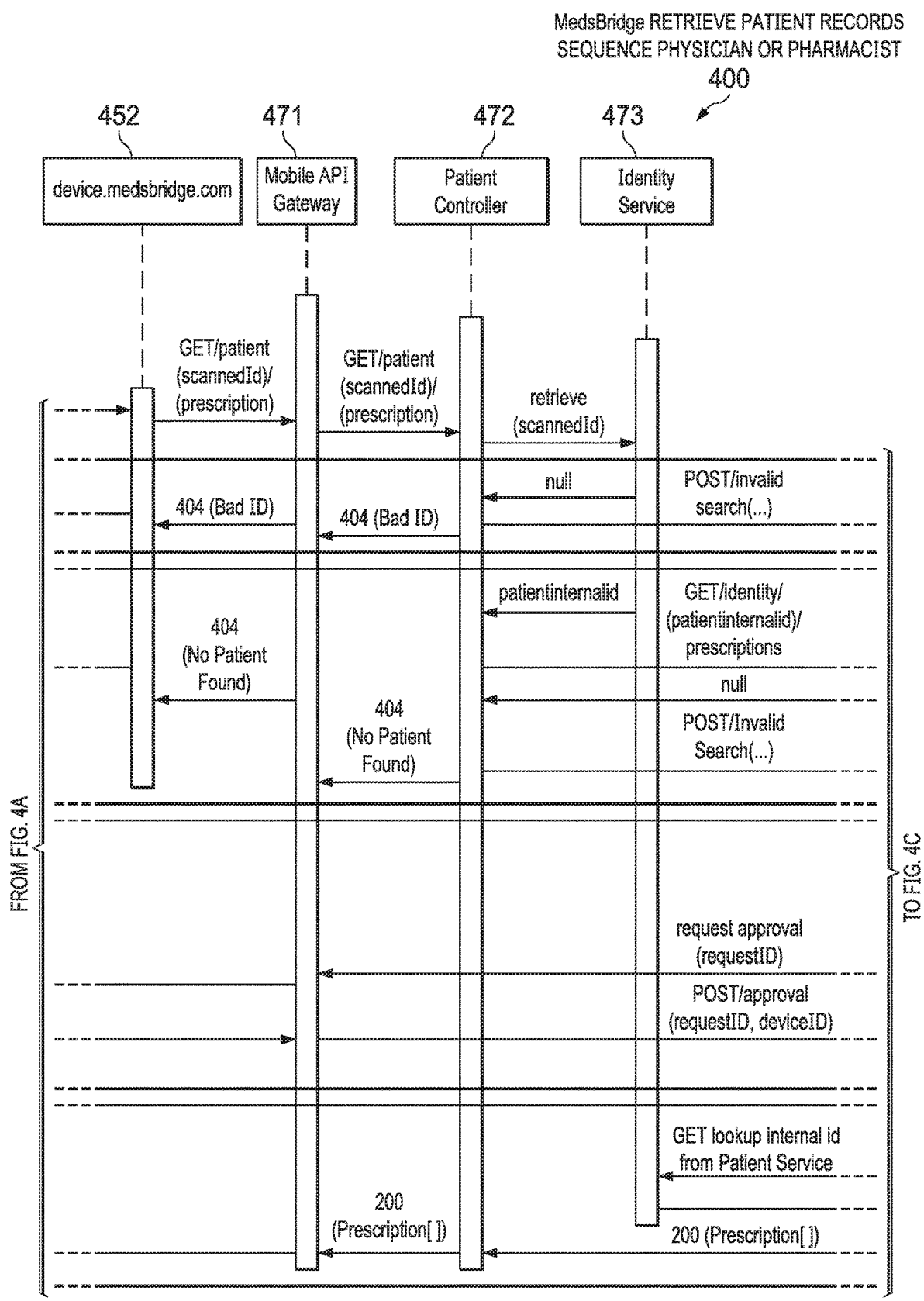
Figure 4C:
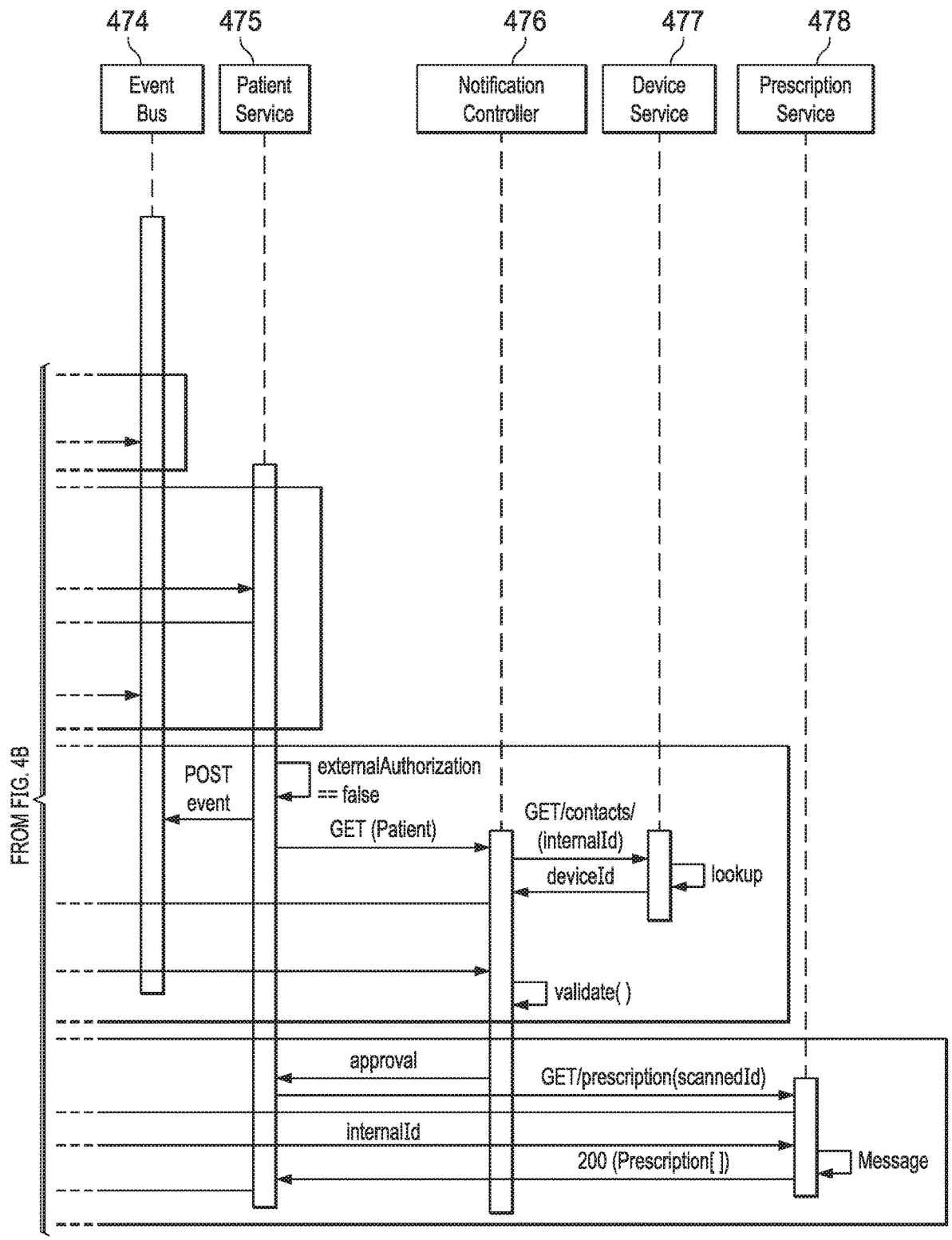

FIGS. 4A, 4B, and 4C show a retrieval of patient record sequence 400 in accordance with embodiments of the disclosure. This sequence 400 may be implemented when a physician or pharmacist wishes to receive a patient's prescription drug record. As shown, information may be authenticated, transmitted, and received via the application 452, the mobile API gateway 471, the patient controller 472, the identity service 473, the event bus 474, the patient service 475, the notification controller 476, the device service 477, and the prescription service 478.

As shown, a patient 404 having a patient app 405 on his or her mobile phone may visit a provider 401 having a reader 402. The provider 401 in the sequence shown may be a healthcare provider or a pharmacist. This sequence may be used to obtain patient records, including prescription drug records, in a secure, compliant, and authenticated manner using the enrolled patient fob 403. The reader 402 may scan the patient fob 403 to receive the scannable ID. The provider may then use the application on the reader 402 to enter one or more pieces of personal information from the patient (e.g., name and date of birth) and/or the patient's prescription information to request the patient medical records associated with the scanned ID from the system application 452. It is contemplated that various combinations of information may be requested from the patient based on the security requirements of the provider. In some embodiments, just the scanned ID may be sent to the system application 452.

This request may be sent through one or more of the mobile API gateway 471 and a patient controller 472. The patient controller 472 may send just the scanned ID to the identity service 473, because the identify service 473 may only have associated scannable IDs and internal IDs. If no record of the scanned ID from the fob exists in the identity service 473, the identity service 473 may transmit back to the patient controller 472 that no ID was found. The patient controller may then utilize an event bus 474 to initiate a sequence for transmitting to the reader 402 that there is no found ID.

If the scannable ID is found at the identity service 473, the identity service 473 may transmit the associated internal ID back to the patient controller 472. The patient controller may then send the information it has, which is now the patient identifying information (from the patient), the internal ID (from the identity service 473), and the prescription information to the patient service 475 to check if there is a valid prescription for the patient stored at the patient service. If the patient is not found, the patient controller 472 may then utilize the event bus 474 to initiate a sequence for transmitting to the reader 402 that no patient is found.

In embodiments, the system may request that the patient approve their entry into the system via the patient application 405. In other embodiments, this step may not be required. In embodiments requiring a patient approval step, the patient may be entered in to the system and found at the patient service, but may not be authorized, If the patient is found at the patient service 475, but the patient is not yet authorized, the patient service 475 may then request an approval from the patient 401 via the patient application 405.

If the patient is found at the patient service 475, the patient service 475 may make a call to a notification controller 476, which sends an approval back to the patient service 475. The notification controller 476 may listen for patient events from the Event Bus. Once an event is received and approved, the notification controller 476 may continue to allow notifications to pass to other components. As shown, an approval from the notification controller 476 allows the patient service 475 to then send the prescription information plus the scanned ID to the prescription service 478. The prescription service 478 then uses the scanned ID to look up the internal ID from the patient service 473 (because the prescription service 478 may not store the scanned ID or the internal ID). The patient service 473 then sends the internal ID to the prescription service 478. Each prescription has a prescription ID, and the prescription service 478 may associate a new prescription ID with and existing patient ID. The prescription service then sends a message with prescription information for that authorized patient back through one or more of the previously described system components to the reader 402.

Figure 5A:
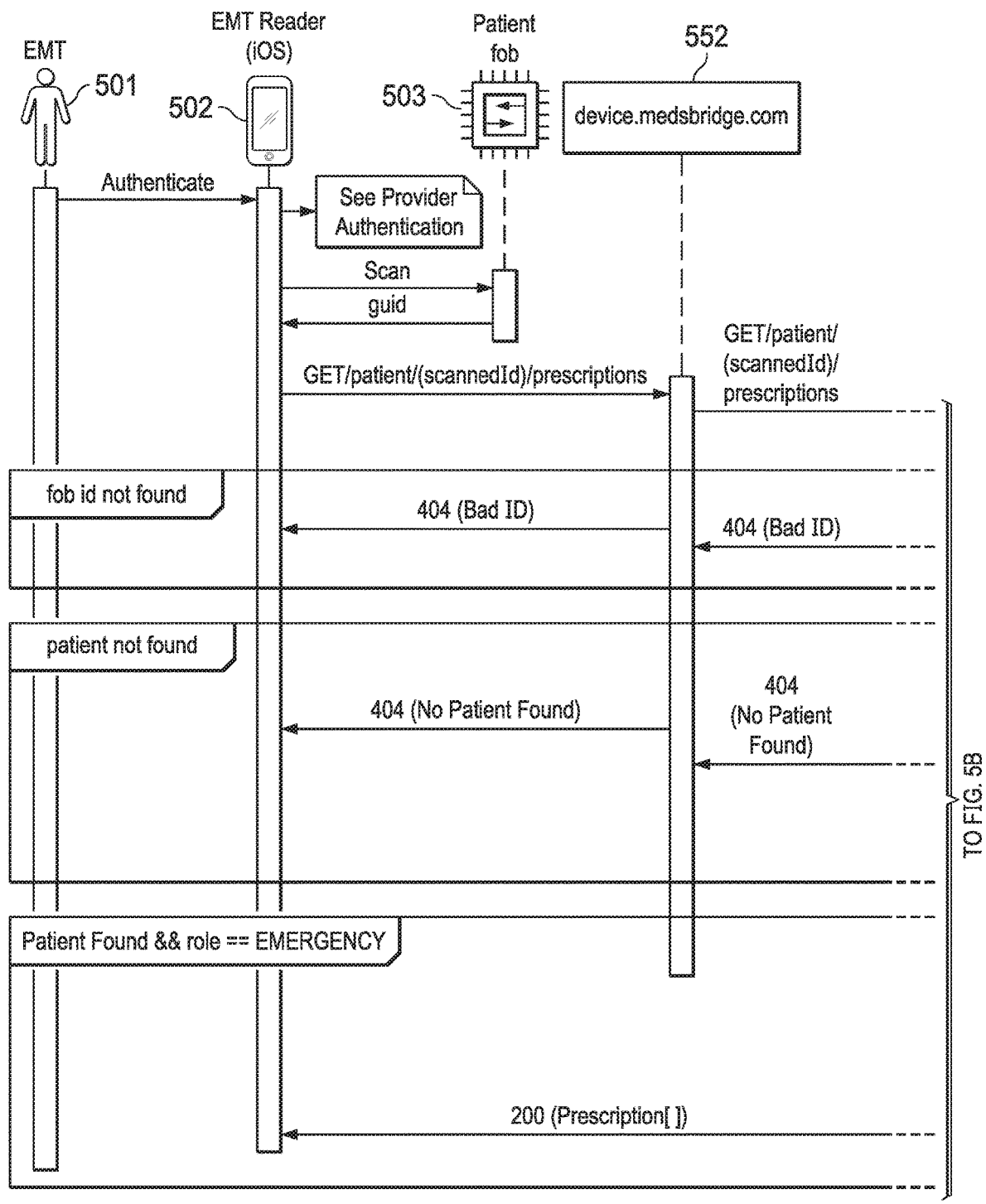
FIGS. 5A, 5B, and 5C show a logical block diagram of a sequence for an emergency medical provider retrieving patient records according to the present disclosure.
Figure 5B:
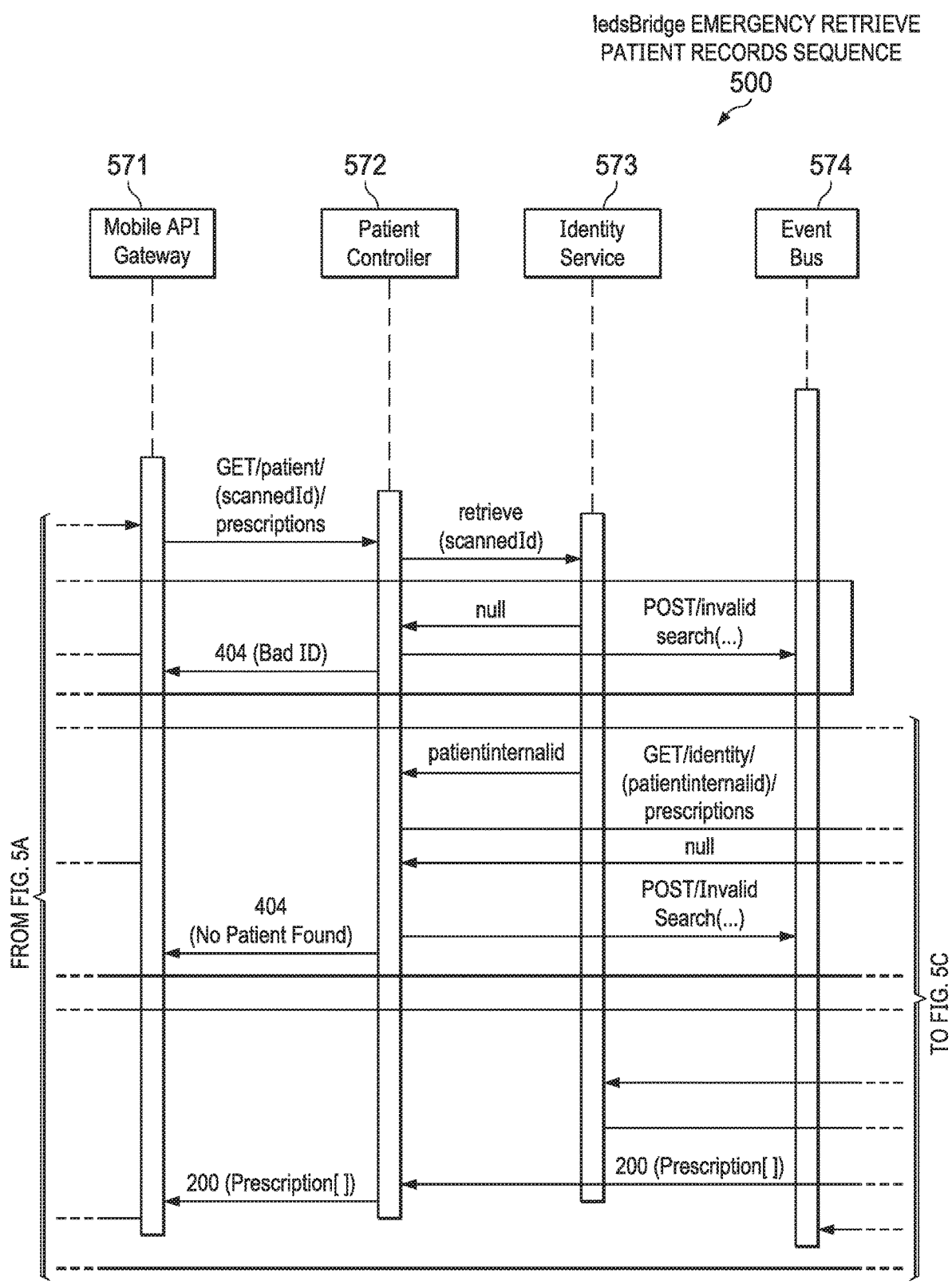
Figure 5C:
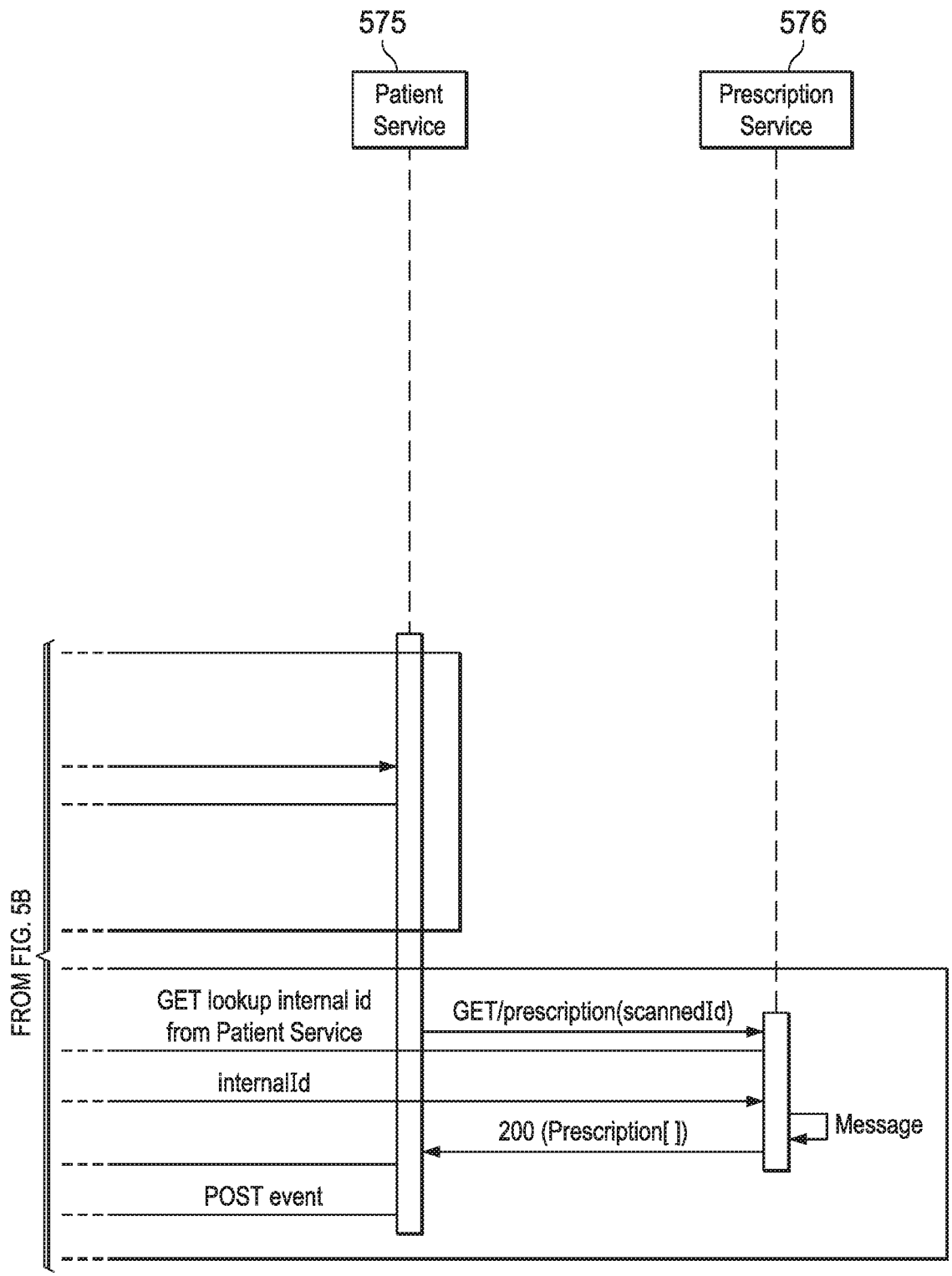

FIGS. 5A, 5B, and 5C show a retrieval of an emergency patient record sequence 500 in accordance with embodiments of the disclosure. This sequence 500 may be implemented when an emergency provider wishes to receive a patient's prescription drug record. As shown, information may be authenticated, transmitted, and received via the application 552, the mobile API gateway 571, the patient controller 572, the identity service 573, the event bus 574, the patient service 575, and the prescription service 576. Each of the various controllers, services, and database in FIGS. 2-5 are implemented to provide legally compliant PHI security, as well as convenience, records redundancy, and accessibility to all stakeholders utilizing the system. The emergency patient record sequence may be simpler than other sequences because the emergency provider may only need to receive prescription information and may not have to enter any information (such as new prescriptions, for example) to send to any of the services of the system.

As shown, an emergency healthcare provider 501 having an emergency reader 502 may scan a patient fob 503 in order to obtain patient records including prescription medication. The emergency provider may authenticate him or herself using one of the methods for provider authentication described in FIGS. 6A and 6B, and the patient fob 503 may send the scannable ID to the emergency reader 502. Similar protocols and transmission sequences as those in FIGS. 2-4 may be implemented, resulting in either a patient fob scannable ID not being found, a patient not being found, or a patient being found and sending the patients prescription information back to the emergency reader 502.

Once the emergency reader 502 has scanned the patient fob 503, the emergency reader 502 may send a request with just the scanned ID to the system application 552, requesting prescription information for the patient associated with the scanned ID. It is contemplated that in emergency situations, the patient may not be conscious or have a family member with them to confirm the patient's personal health information (e.g., name, date of birth, etc.). The system application 552 may send this request to the API gateway 571, which may route the request to the patient controller 572. Then the patient controller 572 may attempt to retrieve a patient internal ID from the identity service 573. If no patient internal ID is associated with the scanned ID, the identity service 573 may send that information to the patient controller 572, which will then relay all the way back to the emergency reader 502 that there is no patient in the system associated with that ID.

If a patient internal ID is associated with the scannable ID at the identity service 573, the identity service 573 may send that patient internal ID to the patient controller 572. The patient controller 572 may not send that information to back to the emergency reader 572 because it is not necessary to provide that information, and because it increases security and the privacy of the patient's health information to not send the information. The patient controller 572 may send the patient internal ID and a request to see if there are any prescriptions associated with the internal ID to the patient service 575. If there are no prescriptions associated, the patient service 575 will send that information to the patient controller 572, which will then relay that no patient prescription was found back to the emergency reader 502.

If at least one prescription is associated with the patient internal ID, the patient service 575 may send a request to get the prescription information from the prescription service 576. The prescription service 576 may then send the prescription information only (e.g., the medication name, dosage, date it was prescribed, etc.) back through the one or more components previously described to the emergency reader 502. This allows the emergency provider 501 to quickly obtain prescription information about the patient, which can help with diagnosing and treating the patient.

FIGS. 6A and 6B show an embodiment of the provider authorization sequence referenced in the previously described sequences. Provider authentication generally functions as an initial security step in the system process to address multiple security and compliance criteria. It may ensure that a healthcare provider is authorized to be enrolled in the system (e.g., by validating the provider's appropriate professional license or prescribing authority), that the provider is associated with an organization (e.g., hospital, pharmacy, or medical office), that the provider fob has not been tampered with, and that the authentication sequence occurs within particular defined parameters (e.g., that the fob, provider, and reader are all in the same physical location, and that it is completed within a certain time). In FIGS. 6A and 6B, the sequence utilizes a provider authentication reader 602 to scan a device fob 603, and information is transmitted in various authentication sequences between the system application 652, the API gateway 671, and an internal security service 672. It is contemplated that other authorization sequences and technologies, including biometric identification, may be used in the provider authentication sequences in embodiments.

Figure 7:
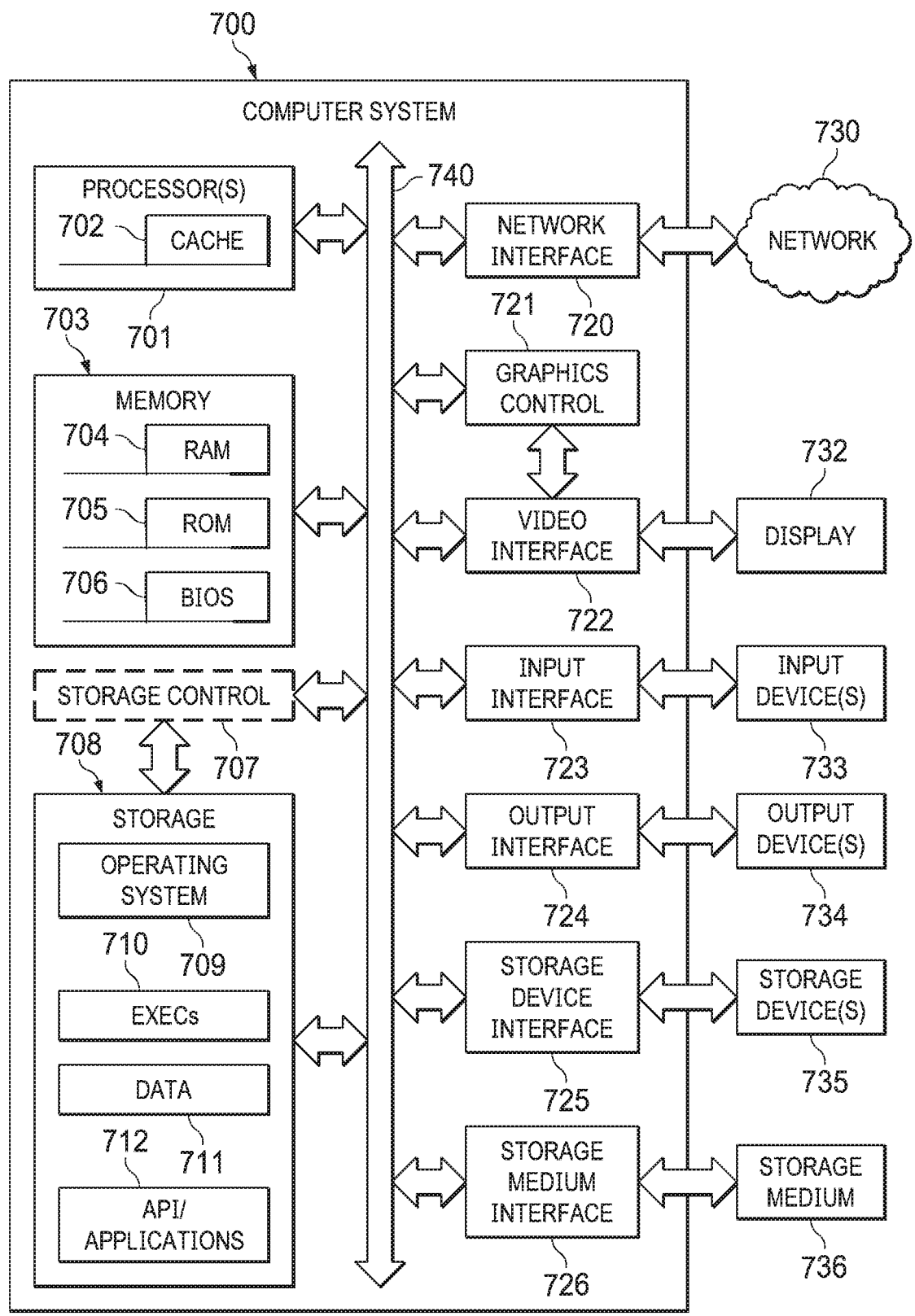
FIG. 7 is a logical block diagram of a computing device that may implement one or more aspects of the present disclosure.

Referring next to FIG. 7, it is a block diagram depicting an exemplary machine that includes a computer system 700 within which a set of instructions can execute for causing a device to perform or execute any one or more of the aspects and/or methodologies of the present disclosure. The components in FIG. 7 are examples only and do not limit the scope of use or functionality of any hardware, software, embedded logic component, or a combination of two or more such components implementing particular embodiments.

Computer system 700 may include a processor 701, a memory 703, and a storage 708 that communicate with each other, and with other components, via a bus 740. The bus 740 may also link a display 732, one or more input devices 733 (which may, for example, include a keypad, a keyboard, a mouse, a stylus, etc.), one or more output devices 734, one or more storage devices 735, and various tangible storage media 736. All of these elements may interface directly or via one or more interfaces or adaptors to the bus 740. For instance, the various tangible storage media 736 can interface with the bus 740 via storage medium interface 726. Computer system 700 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 701 (or central processing unit(s) (CPU(s))) optionally contains a cache memory unit 702 for temporary local storage of instructions, data, or computer addresses. Processor(s) 701 are configured to assist in execution of computer readable instructions. Computer system 700 may provide functionality for the components depicted in FIG. 1 as a result of the processor(s) 701 executing non-transitory, processor-executable instructions embodied in one or more tangible computer-readable storage media, such as memory 703, storage 708, storage devices 735, and/or storage medium 736. The computer-readable media may store software that implements particular embodiments, and processor(s) 701 may execute the software. Memory 703 may read the software from one or more other computer-readable media (such as mass storage device(s) 735, 736) or from one or more other sources through a suitable interface, such as network interface 720. The software may cause processor(s) 701 to carry out one or more processes or one or more steps of one or more processes described or illustrated herein. Carrying out such processes or steps may include defining data structures stored in memory 703 and modifying the data structures as directed by the software.

The memory 703 may include various components (e.g., machine readable media) including, but not limited to, a random access memory component (e.g., RAM 704) (e.g., a static RAM "SRAM", a dynamic RAM "DRAM", etc.), a read-only component (e.g., ROM 705), and any combinations thereof. ROM 705 may act to communicate data and instructions unidirectionally to processor(s) 701, and RAM 704 may act to communicate data and instructions bidirectionally with processor(s) 701. ROM 705 and RAM 704 may include any suitable tangible computer-readable media described below. In one example, a basic input/output system 706 (BIOS), including basic routines that help to transfer information between elements within computer system 700, such as during start-up, may be stored in the memory 703.

Fixed storage 708 is connected bidirectionally to processor(s) 701, optionally through storage control unit 707. Fixed storage 708 provides additional data storage capacity and may also include any suitable tangible computer-readable media described herein. Storage 708 may be used to store operating system 709, EXECs 710 (executables), data 711, API applications 712 (application programs), and the like. Often, although not always, storage 708 is a secondary storage medium (such as a hard disk) that is slower than primary storage (e.g., memory 703). Storage 708 can also include an optical disk drive, a solid-state memory device (e.g., flash-based systems), or a combination of any of the above. Information in storage 708 may, in appropriate cases, be incorporated as virtual memory in memory 703.

In one example, storage device(s) 735 may be removably interfaced with computer system 700 (e.g., via an external port connector (not shown)) via a storage device interface 725. Particularly, storage device(s) 735 and an associated machine-readable medium may provide nonvolatile and/or volatile storage of machine-readable instructions, data structures, program modules, and/or other data for the computer system 700. In one example, software may reside, completely or partially, within a machine-readable medium on storage device(s) 735. In another example, software may reside, completely or partially, within processor(s) 701.

Bus 740 connects a wide variety of subsystems. Herein, reference to a bus may encompass one or more digital signal lines serving a common function, where appropriate. Bus 740 may be any of several types of bus structures including, but not limited to, a memory bus, a memory controller, a peripheral bus, a local bus, and any combinations thereof, using any of a variety of bus architectures. As an example, and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 700 may also include an input device 733. In one example, a user of computer system 700 may enter commands and/or other information into computer system 700 via input device(s) 733. Examples of an input device(s) 733 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 733 may be interfaced to bus 740 via any of a variety of input interfaces 723 (e.g., input interface 723) including, but not limited to, serial, parallel, game port, USB, FIREWIRE, THUNDERBOLT, or any combination of the above.

In particular embodiments, when computer system 700 is connected to network 730, computer system 700 may communicate with other devices, specifically mobile devices and enterprise systems, connected to network 730. Communications to and from computer system 700 may be sent through network interface 720. For example, network interface 720 may receive incoming communications (such as requests or responses from other devices) in the form of one or more packets (such as Internet Protocol (IP) packets) from network 730, and computer system 700 may store the incoming communications in memory 703 for processing. Computer system 700 may similarly store outgoing communications (such as requests or responses to other devices) in the form of one or more packets in memory 703 and communicated to network 730 from network interface 720. Processor(s) 701 may access these communication packets stored in memory 703 for processing.

Examples of the network interface 720 include, but are not limited to, a network interface card, a modem, and any combination thereof. Examples of a network 730 or network segment 730 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 730, may employ a wired and/or a wireless mode of communication. In general, any network topology may be used.

Information and data can be displayed through a display 732. Examples of a display 732 include, but are not limited to, a liquid crystal display (LCD), an organic liquid crystal display (OLED), a cathode ray tube (CRT), a plasma display, and any combinations thereof. The display 732 can interface to the processor(s) 701, memory 703, and fixed storage 708, as well as other devices, such as input device(s) 733, via the bus 740. The display 732 is linked to the bus 740 via a video interface 722, and transport of data between the display 732 and the bus 740 can be controlled via the graphics control 721.

In addition to a display 732, computer system 700 may include one or more other peripheral output devices 734 including, but not limited to, an audio speaker, a printer, and any combinations thereof. Such peripheral output devices may be connected to the bus 740 via an output interface 724. Examples of an output interface 724 include, but are not limited to, a serial port, a parallel connection, a USB port, a FIREWIRE port, a THUNDERBOLT port, and any combinations thereof.

In addition, or as an alternative, computer system 700 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for managing patient medical records, the system comprising:
   a medical records services and database platform, wherein the medical records services and database platform comprises a plurality of separate databases;
   one or more patient physical tracking devices configured to provide a readable scanned identification (scanned ID);
   one or more healthcare provider scanning devices configured to:
     enroll new patients into a medical records services and database platform by:
       entering personally identifying information into an interface of the medical records services and database platform and subsequently scanning the one or more patient physical tracking devices to receive the one or more patient physical tracking device's scanned ID;
     send both the personally identifying information and the scanned ID to a patient database;
     receive an internal ID generated by the patient database of the medical records services and database platform, and
     scan the one or more enrolled patient physical tracking devices;
   and
   one or more pharmacist scanning devices configured to:
     scan the one or more enrolled patient physical tracking devices;
     scan information associated with a medication prescribed to the one or more enrolled patients; and
     associate the internal ID of the one or more enrolled patients with the medication via a prescription service of the medical records services and database platform;
   wherein each of:
     the personally identifying information of the one or more enrolled patients,
     the information associated with a medication prescribed to the one or more enrolled patients, and
     the scanned IDs of the one or more enrolled patient physical tracking devices are each stored in separate databases, wherein:

at least two of the separate databases are located in different remote cloud servers of the medical records services and database platform, thereby creating two or more remote databases; and wherein the scanned IDs and the personally identifying information are associated using the internal ID via an authentication sequence conducted via an identity service that is separate from and between the two or more of the remote databases.

2. The system of claim 1, further comprising:
one or more read-only emergency healthcare provider scanning devices configured to:
  scan one or more of the enrolled patient physical tracking devices to receive the scanned ID, and
  authenticate an identity of the enrolled patient using the scanned ID via the medical records services and database platform; and
  receive personally identifying information and prescription medication information of the enrolled patient from the medical records services and database platform.

3. The system of claim 1, wherein the medical records services and database platform comprises:
one or more secure servers configured to:
  store one or more records of patient health information;
  authenticate requests from any of:
    the one or more physician scanning devices or
    the one or more pharmacist scanning devices; and
  transmit at least one of the one or more records of patient health information to a graphical user interface.

4. The system of claim 1, further comprising:
one or more interfaces configured to:
  display one or more records of patient health information.

5. The system of claim 1, wherein the one or more patient physical tracking devices are read-only devices and the scanned IDs comprise electronically transmittable unique identifiers.

6. The system of claim 5, wherein the one or more patient physical tracking devices comprises a smartphone or tablet configured to be scanned to provide the scanned ID.

7. The system of claim 5, wherein the one or more patient physical tracking devices comprises hardware having embedded software programmed into the hardware.

8. The system of claim 1, wherein the one or more patient physical tracking devices does not comprise any of:
a patient name; and
the patient health information of the one or more enrolled patients.

9. The system of claim 1, wherein the system is compatible with any electronic medical records system.

10. The system of claim 1, further comprising:
one or more healthcare provider physical tracking devices; and
one or more pharmacist physical tracking devices, wherein each of the one or more pharmacist physical tracking device is associated with an individual pharmacist at a particular pharmacy.

11. The system of claim 1, further comprising:
one or more administrator scanning devices, and
one or more administrator physical tracking devices.

12. The system of claim 1, wherein the medical records services and database platform is configured to authenticate authorized access to one or more patient medical records of an enrolled patient by scanning:

one of the one or more enrolled patient physical tracking devices, and one of:
  one or the one or more healthcare provider physical tracking devices, or
  one of the one or more pharmacist physical tracking devices.

13. The system of claim 12, wherein the medical records services and database platform is configured to authenticate authorized access to one or more patient medical records of an enrolled patient by scanning:
a patient biometric identifier.

14. A method for managing patient medical records, the method comprising:
enrolling new patients into a medical records services and database platform, wherein the medical records services and database platform comprises a plurality of separate databases, by:
  entering personally identifying information into an interface of the medical records services and database platform and subsequently scanning the one or more patient physical tracking devices to receive the one or more patient physical tracking device's scanned ID;
  send both the personally identifying information and the scanned ID to a patient database;
  receive an internal ID generated by the patient database of the medical records services and database platform, and
  scanning, with one or more pharmacist scanning devices:
    the one or more enrolled patient physical tracking devices, and
    information associated with a medication prescribed to the one or more enrolled patients; and
  associating the internal ID of the one or more enrolled patients with the medication via a prescription service of the medical records services and database platform;
wherein each of:
  the personally identifying information of the one or more enrolled patients,
  the information associated with a medication prescribed to the one or more enrolled patients, and
  a scanned ID of the one or more enrolled patient physical tracking devices are each stored in separate databases, wherein:
    at least two of the separate databases are located in different remote cloud servers of the medical records services and database platform, thereby creating two or more remote databases; and
    wherein the scanned IDs and the personally identifying information are associated via using the internal ID an authentication sequence conducted via an identity service that is separate from and between the two or more of the remote databases.

15. The method of claim 14, further comprising:
storing one or more records of patient health information;
authenticating, at a secure server, requests from any of:
  one or more physician scanning devices or
  the one or more pharmacist scanning devices; and
  transmitting at least one of the one or more records of patient health information to a graphical user interface.

16. The method of claim 14, further comprising:
authenticating authorized access to one or more patient medical records of an enrolled patient by scanning:

one of the one or more enrolled patient physical tracking devices, and one of:
one or the one or more healthcare provider physical tracking devices, or
one of the one or more pharmacist physical tracking devices.

17. The method of claim 16, further comprising:
authenticating authorized access to one or more patient medical records of an enrolled patient by scanning a patient biometric identifier.

18. The method of claim 16, further comprising:
displaying, based on the authentication, one or more patient medical records on a user interface.

19. The method of claim 14, further comprising:
storing the personally identifying information about the enrolled patient in a first database, the prescribed medication of the enrolled patient in a second database, and an internal ID and scanned ID associated with the enrolled patient in a third database within the medical records services and database platform.

20. The method of claim 14, further comprising:
providing a portal to each of a healthcare provider and a pharmacist, the portal configured temporarily display a prescription drug history of one or more of the enrolled patients.

* * * * *